(12) United States Patent
Hirshman

(10) Patent No.: US 8,728,010 B2
(45) Date of Patent: May 20, 2014

(54) ELONGATE MEDICAL DEVICE INCLUDING DEFORMABLE DISTAL END

(75) Inventor: Peter Hirshman, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 536 days.

(21) Appl. No.: 11/509,185

(22) Filed: Aug. 24, 2006

(65) Prior Publication Data
US 2008/0077049 A1 Mar. 27, 2008

(51) Int. Cl.
*A61M 25/00* (2006.01)
*A61M 25/09* (2006.01)

(52) U.S. Cl.
CPC ............. *A61M 25/09* (2013.01); *A61M 25/008* (2013.01); *A61M 2025/09133* (2013.01); *A61M 2025/09141* (2013.01); *A61M 25/0051* (2013.01)
USPC ....................................... 600/585

(58) Field of Classification Search
USPC ....................................... 600/585
See application file for complete search history.

(56) References Cited

U.S. PATENT DOCUMENTS

| | | | | |
|---|---|---|---|---|
| 4,665,906 A | * | 5/1987 | Jervis | 606/78 |
| 4,925,445 A | * | 5/1990 | Sakamoto et al. | 604/528 |
| 5,190,546 A | * | 3/1993 | Jervis | 606/78 |
| 5,238,004 A | * | 8/1993 | Sahatjian et al. | 600/585 |
| 5,597,378 A | | 1/1997 | Jervis | |
| 5,697,906 A | | 12/1997 | Ariola et al. | |
| 5,746,701 A | * | 5/1998 | Noone | 600/585 |
| 5,772,609 A | | 6/1998 | Nguyen et al. | |
| 5,876,434 A | | 3/1999 | Flomenblit et al. | |
| 6,004,279 A | * | 12/1999 | Crowley et al. | 600/585 |
| RE36,628 E | * | 3/2000 | Sagae et al. | 148/537 |
| 6,068,623 A | * | 5/2000 | Zadno-Azizi et al. | 604/530 |
| 6,190,332 B1 | * | 2/2001 | Muni et al. | 600/585 |
| 6,428,489 B1 | | 8/2002 | Jacobsen et al. | |
| 6,488,637 B1 | * | 12/2002 | Eder et al. | 600/585 |
| 6,508,803 B1 | | 1/2003 | Horikawa et al. | |
| 6,579,246 B2 | * | 6/2003 | Jacobsen et al. | 600/585 |
| 6,592,570 B2 | | 7/2003 | Abrams et al. | |
| 6,610,046 B1 | * | 8/2003 | Usami et al. | 604/530 |
| 6,669,670 B1 | * | 12/2003 | Muni et al. | 604/164.13 |

(Continued)

FOREIGN PATENT DOCUMENTS

| | | |
|---|---|---|
| EP | 1105181 B1 | 6/2001 |
| EP | 1426071 A2 | 6/2004 |
| WO | 02/087483 A1 | 11/2002 |
| WO | 03/039623 A2 | 5/2003 |

*Primary Examiner* — Sean Dougherty
*Assistant Examiner* — Michael C Stout
(74) *Attorney, Agent, or Firm* — Seager, Tufte & Wickhem LLC

(57) ABSTRACT

An intracorporeal device includes an elongate tubular member. The tubular member can comprise one or more materials that have superelastic and/or shape memory characteristics. The tubular member can comprise one or more deformable zones and one or more elastic zones. The deformable zone(s) can comprise material(s) that are less elastic than the material in the elastic zone(s). The deformable and elastic zones can contain different materials or they can contain the same or similar materials that have been treated in order to change the elasticity or type of elasticity of one of the zones relative to the other zones, creating different elasticity between the elastic and the deformable zones. The intracorporeal device can be, for example, a guidewire, a catheter or any other intracorporeal device that can include an elongate tubular member.

32 Claims, 7 Drawing Sheets

(56) References Cited

U.S. PATENT DOCUMENTS

| | | |
|---|---|---|
| 6,918,882 B2 | 7/2005 | Skujins et al. |
| 7,632,303 B1 * | 12/2009 | Stalker et al. ............ 623/1.19 |
| 2001/0039412 A1 | 11/2001 | Fariabi |
| 2002/0128677 A1 * | 9/2002 | Duerig et al. ............ 606/198 |
| 2003/0069521 A1 | 4/2003 | Reynolds et al. |
| 2003/0069522 A1 * | 4/2003 | Jacobsen et al. ............ 600/585 |
| 2003/0120181 A1 * | 6/2003 | Toma et al. ............ 600/585 |
| 2003/0125709 A1 | 7/2003 | Eidenschink |
| 2004/0142643 A1 | 7/2004 | Miller et al. |
| 2004/0167437 A1 | 8/2004 | Sharrow et al. |
| 2004/0167441 A1 | 8/2004 | Reynolds et al. |
| 2004/0210163 A1 * | 10/2004 | Osawa et al. ............ 600/585 |
| 2005/0124917 A1 * | 6/2005 | Skujins et al. ............ 600/585 |
| 2005/0137501 A1 * | 6/2005 | Euteneuer et al. ............ 600/585 |
| 2005/0267444 A1 * | 12/2005 | Griffin et al. ............ 604/525 |
| 2006/0100693 A1 * | 5/2006 | Walak et al. ............ 623/1.18 |
| 2006/0189896 A1 * | 8/2006 | Davis et al. ............ 600/585 |
| 2007/0049902 A1 * | 3/2007 | Griffin et al. ............ 604/523 |
| 2007/0100285 A1 * | 5/2007 | Griffin et al. ............ 604/164.11 |

\* cited by examiner

ELONGATE MEDICAL DEVICE INCLUDING DEFORMABLE DISTAL END

TECHNICAL FIELD

The invention pertains generally to elongate medical devices such as catheters, guidewires, and the like. More specifically, the invention pertains to tubular structures within such medical devices.

BACKGROUND

A wide variety of medical devices such as catheters and guidewires have been developed. Medical devices such as catheters and guidewires can be used for performing intravascular procedures. These intravascular procedures have become commonly used in order to avoid more invasive surgical procedures. Because the anatomy of a patient may be very tortuous, it can be desirable to have particular performance features in an elongate medical device. A number of different structures and assemblies for elongate medical devices such as catheters and guidewires are known, each having certain advantages and disadvantages. However, there is an ongoing need to provide alternative structures and assemblies.

SUMMARY OF SOME EMBODIMENTS

The invention provides several alternative designs, materials and methods of manufacturing and use of alternative medical device structures and assemblies.

Accordingly, an example embodiment can be found in an intra-luminal or intracorporeal medical device including a tubular member. The tubular member can have proximal and distal portions and can have one or more zones of metal alloy, for example Nitinol. One or more of these zones of metal alloy can comprise an alloy with superelastic and/or shape memory characteristics that has austenitic and martensitic states. The alloy in each zone can have a temperature, $A_f$, above which the tubular member may assume the austenitic state. One zone of the tubular member can have one $A_f$, and a second zone can have a second, higher $A_f$. The tubular member can comprise one alloy along the length of the tubular member, with the alloy of the distal portion conditioned or treated to raise the $A_f$ from an initial $A_f$ temperature to a second, higher $A_f$ temperature. The initial $A_f$ can be below the temperature of use and the second $A_f$ temperature can be above the temperature of use. For example, the temperature of use can be the normal body temperature of a human body, or 37° C., or it can be higher than body temperature, such as 42° C. The temperature of use can also be a range, for example 10° C. to 45° C. The intracorporeal devices of this example can be guidewires, catheters, or any other elongate medical device that comprise tubular members.

Another example embodiment can have a tubular member, for example any of the tubular members of the previous paragraph, and can further comprise a core member. The core member can be of a solid cross-section, and at least a portion of the core member can be disposed in a lumen defined by the tubular member. A proximal portion of the tubular member can be attached to the core member at a point of attachment and can extend distally around the core member from this point of attachment. The core member can comprise a metal such as stainless steel.

Another embodiment can comprise a method of making and/or using an elongate medical device. In one method of manufacture, a tubular member can be provided. In another method of manufacture, a core member and a tubular member can be provided, and the core member can be disposed at least partially inside a lumen of the tubular member. A proximal portion of the tubular member can be attached to the core member. Further, during manufacture or during use, the distal portion of the tubular member can be treated to raise the $A_f$ of the distal portion, in some cases above 42° C. Also, in an example method of manufacture or use, the shape of the distal portion of the tubular member with a higher $A_f$ can be changed from a first shape to a second shape and the distal portion can substantially remain in the second shape.

The above summary of some embodiments is not intended to describe each disclosed embodiment or every implementation of the present invention. The Figures, and Detailed Description which follows, more particularly exemplify these and other embodiments.

BRIEF DESCRIPTION OF THE FIGURES

The invention may be more completely understood in consideration of the following detailed description of various embodiments of the invention in connection with the accompanying drawings, in which.

Figure 2:
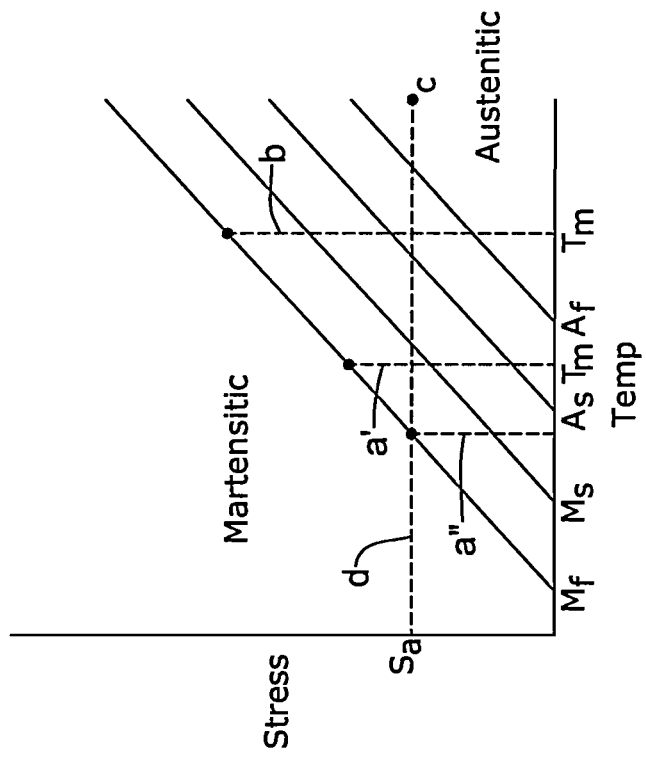
FIG. 2 is a graph of the critical temperature and stress curves of a typical metal alloy having austenitic and martensitic states.

While the invention is amenable to various modifications and alternative forms, some specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

For example, although discussed with specific reference to guidewires and catheters in the particular embodiments described herein, the invention may be applicable to a variety of medical devices that are adapted to be advanced into the anatomy of a patient through an opening or lumen. For example, the invention may be applicable to fixed wire devices, a variety of catheters (e.g., balloon, stent delivery, etc.) drive shafts for rotational devices such as atherectomy catheters and IVUS catheters, endoscopic devices, laproscopic devices, embolic protection devices, spinal or cranial navigational devices, and other such devices. Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

The devices of the current invention can comprise an elongate medical device, and the medical device can have a tubular member. Different medical device structures and uses will be described below. The shaft, and in particular the tubular member, can comprise one or more materials that exhibit shape memory or superelastic behavior, or both. These materials can be metal alloys, for example Nitinol.

In general, certain Nitinol alloys can exhibit shape memory or superelastic (or pseudoelastic) behavior, or both. Although Nitinol is essentially a binary alloy with Nickel and Titanium, some superelastic and/or shape memory Ni:Ti alloys can contain additional elements, such as Cobalt or Vanadium. In addition, some other alloys exhibit shape memory or superelastic behavior or, like some Ni:Ti alloys, both shape memory and superelasticity. Some examples of these alloys are: AgCd, AuCd, AuCu, CuAlNi, CuAuZn, CuSn, CuZn, CuZnSi, CuZnSn, CuZnAl, CuZnGa, CuZnXe, CuAlNi, InTl, NiAl, FePt, FePd, FeMn, $Fe_3Be$, $Fe_3Pt$, FeNiTiCo, and MnCu. Some polymers and other materials have also been shown to exhibit shape memory or superelastic behavior, or both.

Although superelasticity and shape memory characteristics can be interrelated, the concepts are separate physical phenomena. Superelasticity is a sub-category of elasticity, and in some ways can be contrasted with linear elasticity, whereas shape memory is generally the ability of a material to be deformed, remain deformed, and later assume the initial shape. Without being constrained by the theories presented herein, these concepts will be described in greater detail below.

Figure 1:
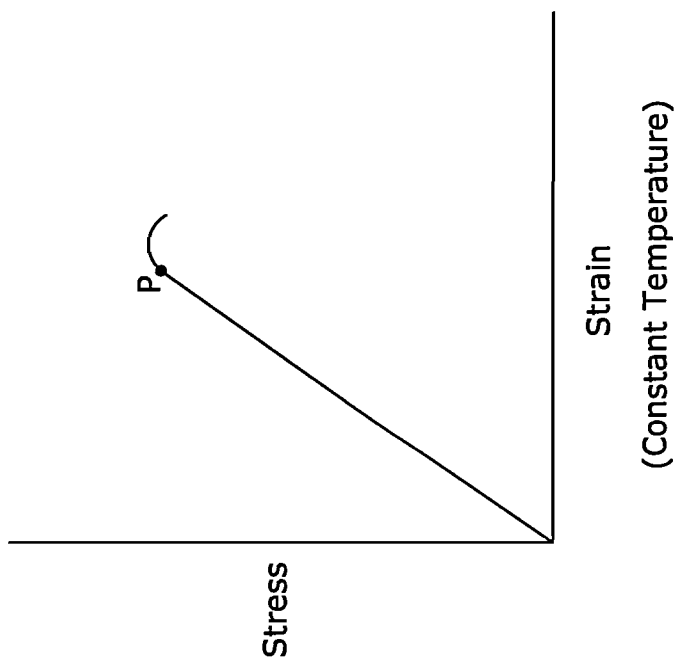
FIG. 1 is a graph of a stress-strain curve of a typical linear elastic material.

Referring to FIG. 1, when stress is applied to linear elastic materials at a relatively constant rate, the stress-strain curve can initially be linear until the material reaches its proportional limit (shown at point P). If stress is further applied to the material after this point, the material can be plastically deformed, and the material may not return to its original shape and size when the stress is removed. Thus, with linear elastic materials, the stress-strain curve appears as a substantially straight line within the proportional region (the portion of the curve before the proportional limit). When the material is stressed within this proportional region, the strain can increase proportionally, and when the stress is removed, the strain may decrease substantially along the same straight line, substantially back to the origin of the stress-strain graph.

In the case of superelastic metal alloys (SEMAs), the stress-strain curve can be non-linear. This non-linearity can be a product of a phase change that occurs within the alloy when the alloy is being subjected to stress (as opposed to linear elastic materials, which generally do not have a phase change within the elastic region). Some SEMAs can have two solid-state phases that are relevant to superelasticity: the austenite phase and the martensite phase. The austenite phase can be the higher energy, stronger phase of these alloys, and the martensite phase can be the lower energy, more deformable phase. The change between these phases can cause a change in the crystal structure of the metal. Two common catalysts for the change between these phases can be thermal changes and stresses applied to the material. These mechanisms will be discussed further below.

FIG. 2 shows the phases present at given stress and temperature combinations for an example SEMA. In general, there can be four lines of interest relating to the phase changes that occur within a SEMA. The lines $A_s$ and $A_f$ can denote the austenite start and austenite final, which can be the temperature and load combinations at which the SEMA starts and finishes, respectively, the transformation from the martensitic state to the austenitic state. Likewise, the $M_s$ and $M_f$ can be the temperature and load combinations at which a SEMA starts and finishes the transformation from an austenitic state to a martensitic state. In this Figure, these lines are shown as $M_f < M_s < A_s < A_f$. In the case of some materials, these lines could be in a different order, for example $M_f < A_s < M_s < A_f$.

If the temperature of the example SEMA is held constant and a stress is placed on the SEMA, the SEMA may undergo a phase transformation between austenitic and martensitic states. This transformation is called a stress-induced martensitic transformation. For example, the line (b) in FIG. 2 shows the material being subjected to stress where the $T_m$ (temperature of the material) is greater than the $A_f$ temperature of the material. Because the temperature of the material is above the $A_f$ temperature, it is entirely in its austenitic form before stress is applied. As stress is applied to the material, it reaches the line $M_s$, where a martensitic crystal structure begins to form. Further along line (b) the line $M_f$ is reached. At this point, the SEMA is fully martensitic. When the stress is removed from the SEMA, it returns to its former austenitic state (and, in the process, substantially to its original shape) along the same line (b). With the temperature of the material being greater than the $A_f$ temperature, the crystal structure of the material will be driven toward the austenitic state in the absence of stress. When the SEMA passes across the line $A_s$, the austenitic crystal structure begins to form, and the material is fully austenitic when it passes across the line $A_f$.

Figure 3:
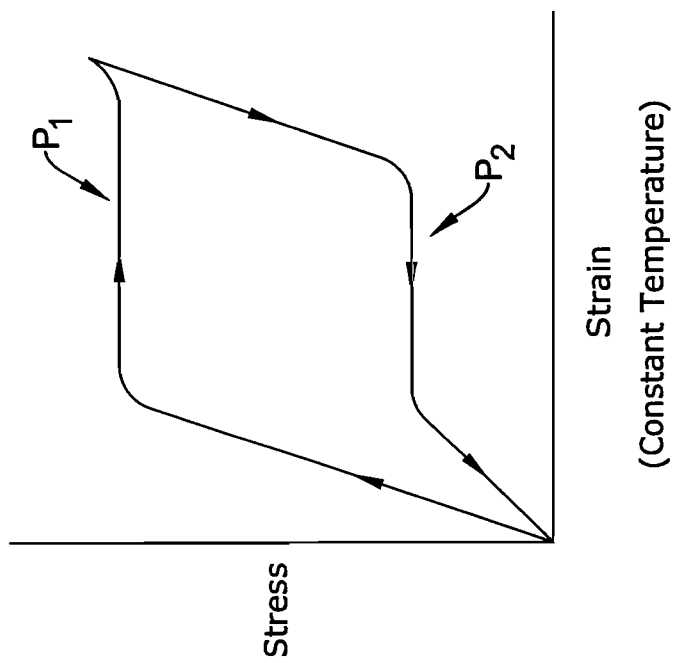
FIG. 3 is a graph of s stress-strain curve of a typical superelastic alloy.

If the stress cycle described in the above paragraph is plotted on a stress-strain curve where the $T_m$ is above the $A_f$ temperature, the curve can look like FIG. 3. As depicted in FIG. 3, the curve has an initial steep slope on the extension portion of the curve, followed by a plateau region (marked $P_1$) which can be the region of phase change between the austenitic and martensitic phases. The curve also has an additional plateau region (marked $P_2$) on the return portion of the curve, which can be the region of phase change between the martensitic and austenitic forms. These plateau regions are regions where the example SEMA can undergo significant deformation without being subjected to large amounts of stress (the slope of the curve is very shallow). These plateau regions are often a desirable attribute of superelastic materials because little stress is required in order to deform the material in this region of the curve, and the material may also return to its initial shape, as shown by the return portion of the curve in FIG. 3.

As can be observed from FIGS. 2 and 3, it can be the presence of the two solid-state phases of the SEMA which drive the SEMA to be superelastic, or to be able to return to its original shape and/or size once it has been deformed. If the $T_m$ is above $A_f$ temperature (as shown by line (b) in FIG. 2), then the SEMA, once a stress is applied and removed, can return along the line (b) in FIG. 2 (corresponding to the return portion of the curve in FIG. 3). As long as the $T_m$ is above the $A_f$ temperature, when the stress is removed, the crystal structure can return to its original austenitic state, including its original shape and size. This tendency to return to its original configuration is correctly referred to as superelasticity. (It is sometimes incorrectly referred to in the art as a shape memory characteristic of this material because the material can "remember" (and return to) its original shape. However, shape memory will be further explained below.) Because of the phase change in the material and the resultant shape of the stress-strain curve, these elastic materials are called superelastic or pseudoelastic (as opposed to linear elastic).

Shape memory, on the other hand, can refer to the ability of a material to be deformed from a first to a second shape, to maintain the second shape when the stress is removed, then to return to the first shape when the material is subjected to an additional catalyst, for example changes in the temperature of the material ($T_m$).

Referring again to FIG. 2, a shape memory alloy (SMA) such as certain Nitinol alloys can be in a first shape when the SMA is above the $A_f$ temperature (for example, see point (c)), then the material can be cooled down below the $M_f$ temperature, making the SMA fully martensitic. For example, this cooling can be along the line (d) in FIG. 2, which depicts a constant-stress being placed on the material (this could also be depicted along the temperature axis of FIG. 2, which would be a constant stress level of zero; for simplicity, it is depicted at a constant, elevated stress). The martensitic form of the SMA can be more easily deformable compared to the austenitic form, and the material can be formed into a second shape. The SMA may be able to maintain this second shape as long as it is in the martensitic form. Later, if the material is heated back through the $A_s$ temperature above the $A_f$ temperature (again, as shown along line (d) in FIG. 2), the material can reform the first shape. The cycle can be repeated with the material being cooled back below the $M_f$ temperature and deformed once again, again returning to the first shape when the material is returned to a temperature above the $A_f$ temperature. This is called a one-way shape memory material because the transformation is one-way; the one-way material does not change shape when cooled to form martensite, but must be deformed into the second shape by an outside force.

Also possible are two-way shape memory materials that assume one shape upon cooling of the material and another shape upon heating of the material.

From the above discussion, it becomes apparent that changing the temperature ($T_m$) of a SMA or SEMA can change the characteristics of the material. For example, a metal alloy that has both shape memory and superelastic characteristics and austenitic and martensitic states and has a given $A_f$ temperature may not exhibit shape memory characteristics if the alloy is maintained above the $A_f$ temperature. Placing the material under a stress may simply form stress-induced martensite, and the release of the stress may allow the material to return to the austenitic phase. Thus, this material at these conditions may not have shape memory characteristics, but it may have superelastic characteristics. (Again, such a scenario is shown with line (b) in FIG. 2 and in FIG. 3.)

Figure 4:
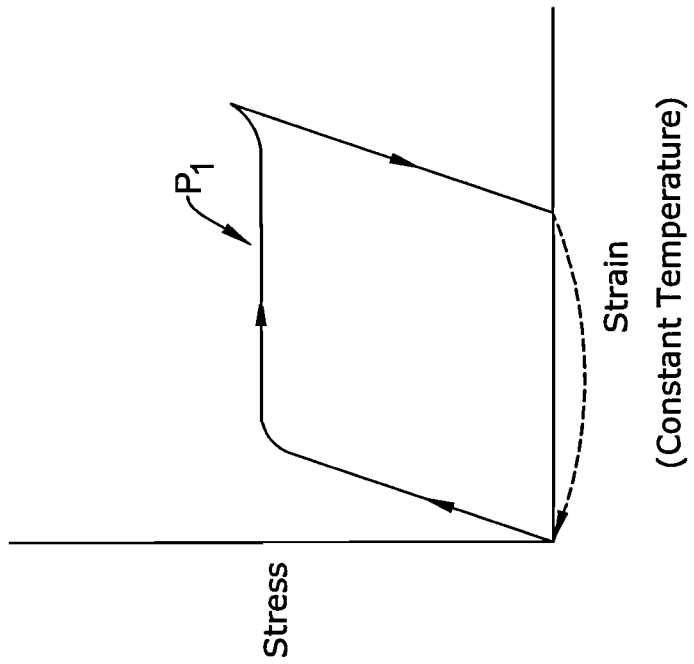
FIG. 4 is a graph of a stress-strain curve of a typical shape memory alloy.

Further, if a material is fully austenitic (for example, if it was initially raised above the $A_f$ temperature, forming the austenite crystal structure) and it is later lowered to, and maintained at a temperature below the $A_f$ temperature, then a stress placed on the material can cause the formation of martensite crystal structure, but the removal of the stress may not cause the entire crystal structure to return to the austenitic phase. Because there is not a full return to the initial austenitic phase, the material may not make a full return of the initial strain. In other words, the material may remain at least partially deformed. Examples of such a scenario are shown with lines (a') and (a") in FIG. 2. (Some austenite could be formed, and thus some strain and shape returned, if the $T_m$ is above $A_s$ temperature, as shown with line a' in FIG. 2.) The stress-strain curve of such a scenario is shown with a solid line in FIG. 4. However, the shape memory characteristics of these materials can cause the material to return to the initial shape and size if the material is subsequently heated above the $A_f$ temperature. This return is shown with a dotted line in FIG. 4, and can be driven by the phase change from the martensitic to the austenitic phase as the $T_m$ is increased above the $A_s$ temperature and the $A_f$ temperature. Thus, this material can show relatively weak elastic characteristics if the $T_m$ is below the $A_f$ temperature (although it can show some elastic characteristics if the $T_m$ is above the $A_s$ temperature). However, such a material in these conditions can still exhibit shape memory characteristics if the material is subsequently heated to form the austenitic phase and return the material to the first shape. In either case (superelastic behavior or shape memory behavior), the return of a material to the original shape and/or the return of strain can be driven by the phase change between martensite and austenite in the material.

There are several common ways to change the critical temperatures of $M_f$, $M_s$, $A_s$ and $A_f$ and/or remove superelasticity and/or shape memory characteristics from a SEMA/SMA. First, the composition of the alloy can have an effect on these critical temperatures. With Nitinol, changing the ratio of Ni:Ti can affect the critical temperatures, or can even make the Nitinol lack superelastic and shape memory characteristics altogether. For example, some common Ni:Ti superelastic and/or shape memory alloys have compositions in range of 49-51% Nickel. In other examples, a Ni:Ti alloy can contain 49%-55% Nickel.

Also, within the family of commercially available Nitinol alloys is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there are no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy for a proximal or distal portion of a medical device allows the medical device to exhibit superior "pushability" around tortuous anatomy.

In some embodiments, the linear elastic nickel-titanium alloy comprises in the range of about 50 to about 60 wt. % nickel, with the remainder being essentially titanium. In some particular embodiments, the composition comprises in the range of about 54 to about 57 wt. % nickel. One example of a suitable nickel-titanium alloy is FHP-NT alloy commercially available from Furukawa Techno Material Co. of Kanagawa, Japan. Some examples of nickel-titanium alloys are disclosed in U.S. Pat. Nos. 5,238,004 and 6,508,803, which are herein incorporated by reference.

In varieties of Nitinol that exhibit shape memory and/or superelastic behavior, adding other elements to the Ni:Ti alloy can also change the alloy properties. Further, other alloys, polymers or other types of materials can be used to form superelastic and/or shape memory alloys. The ratios of elements in many other shape memory or superelastic alloys can also be varied in order to affect these critical temperatures. In addition and as shown in FIG. 2, the shape memory and/or superelastic behavior can be changed by changing the load (stress) on these materials.

Further, the preparation of the alloy can also affect the critical temperatures. For example, with some forms of Nitinol, exposing the alloy to a high temperature tends to raise the critical temperature points. In one example, the $A_f$ temperature of 49.8% Ti Nitinol can be raised from 30° C. to 37° C. by annealing the alloy at 500° C. for one hour when compared to heating the alloy at 400° C. for one hour. In some examples, the portion of the alloy in which the critical temperatures are to be altered is heated above 500° C. for a period of time in order to change the critical temperatures. Alternatively, the alloy can be heated above 550° C. or 600° C. The amount of time that the alloy structure must be exposed to the heat will vary with the type of structure. Using DSC or DMTA analysis, one of skill in the art can determine if the critical temperatures has been altered to the degree required for the application. The deformability (as opposed to elasticity) at certain temperatures can also be an indication that the critical temperatures have been sufficiently modified. Sources of heat can include a sand bath, a conventional oven with heat shielding for a portion of the device, or heating coils that can expose a zone of the device to the required amount of thermal energy. Persons of ordinary skill in the art will appreciate that other methods of heating all or a portion of the alloy can also be effective in changing the critical temperatures of the alloy.

Shape memory and superelastic materials can be incorporated into medical devices in different ways. For example, an elongate structure can have a tubular member. The tubular member can have several zones along its length, where the zones can have different properties. In one embodiment, the tubular member can be made from a single material that exhibits shape memory and/or superelastic properties. Examples can be any of the materials mentioned above, for example metal alloys such as Nitinol. The material can be treated or otherwise incorporated into the device in such a manner as to cause a distal end of the device to have superelastic or shape memory characteristics at different conditions at different zones of the elongate structure. For example, with a metal alloy such as Nitinol, this could be accomplished by raising the $A_s$ temperature, the $A_f$ temperature, or both, of one zone above the $T_m$ (as used herein, the $T_m$ can be the temperature of use or the range of temperatures in which the material may be used) and maintaining the $A_s$ temperature, the $A_f$ temperature, or both, of a second zone below the $T_m$. Thus, a second, proximal zone of the tubular member can still exhibit superelastic behavior at the $T_m$ or within the range of temperatures in which the tubular member may be used. With such a structure, a first, distal zone of the tubular member may be deformable and/or exhibit linear elastic behavior at or within the $T_m$, while a second, proximal zone of the tubular member may still exhibit superelastic properties.

Other embodiments may also have the $M_f$ temperature and/or the $M_s$ temperature of the first zone raised above the use $T_m$ and maintain the $M_f$, $M_s$, $A_s$, and/or the $A_f$ temperatures or any combination thereof, of the second zone below the $T_m$. In addition, another embodiment can have different alloys in the different zones of the tubular member, with the different alloys having the same possible combinations of properties as the different treated portions described above. Other types of material configurations will also be discussed below, along with some specific examples of these types of structures and methods of manufacture and use of such structures.

Figure 5:
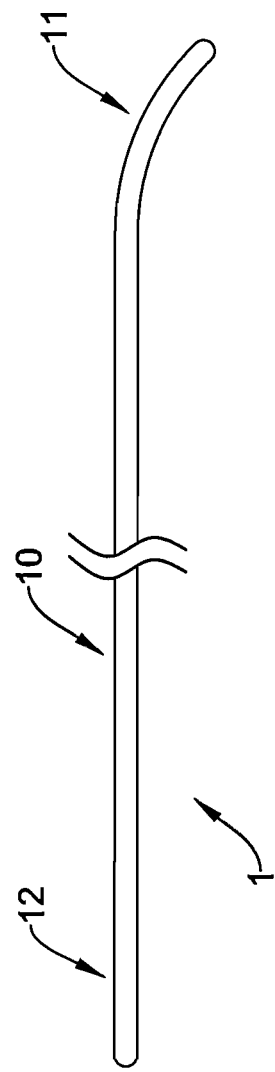
FIG. 5 is a perspective view of one embodiment of a guidewire.

Refer now to FIG. 5, which is a perspective view of a guidewire 1. The guidewire can have a shaft 10 with a proximal end 12 and distal end 11. The guidewires described in this application can be used in a variety of procedures. The guidewires can be shaped and configured to be inserted into a body lumen, such as the vasculature, of a patient. Another device such as a catheter can then be advanced over the guidewire to a point of interest within the patient's vasculature. The guidewires can also be advanced through a catheter that is in place in a patient's vasculature. In addition, the guidewires can have devices disposed along the length of the guidewire such as balloons, atherectomy devices or other devices known in the art for performing intravascular procedures. The guidewires can also have lumens extending along all or a portion of the length of the guidewires, allowing other devices or elements to be passed through the lumen(s) and/or allowing fluid communication through all or a portion of the length of the guidewire.

Figure 6:
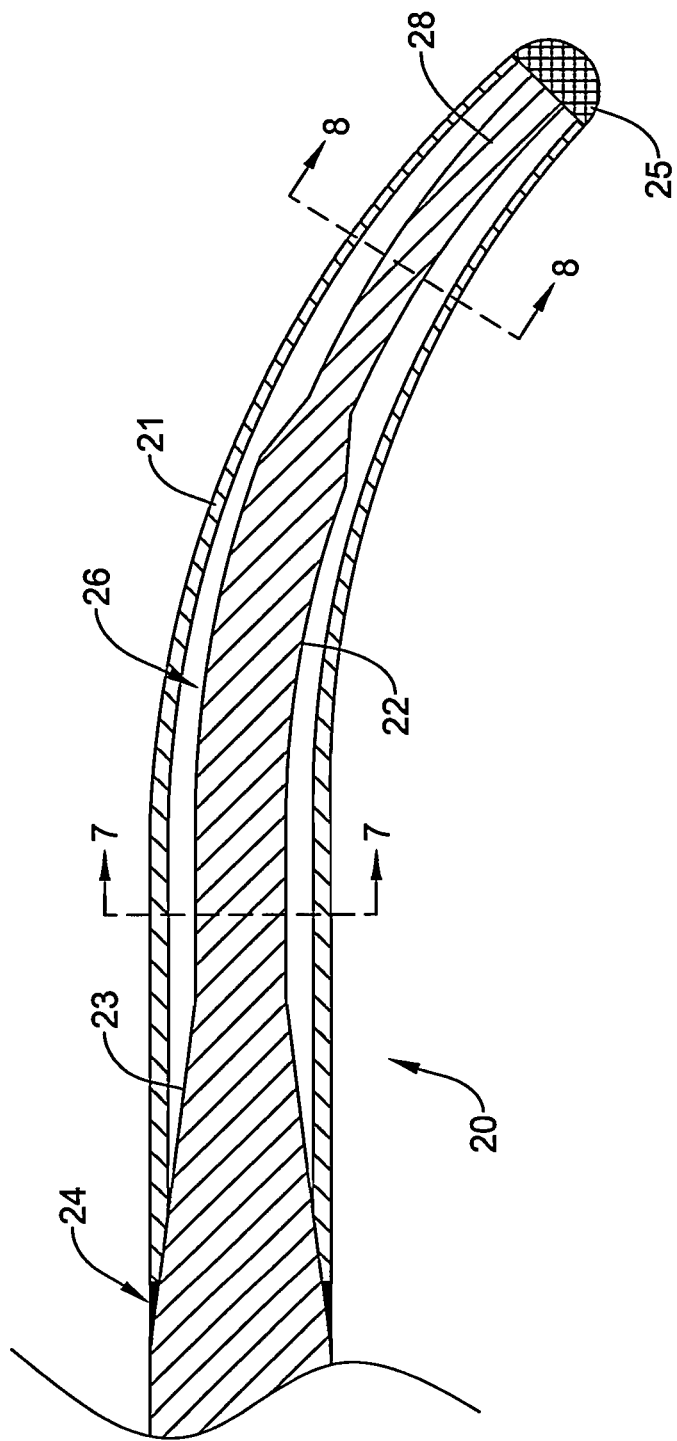
FIG. 6 is a longitudinal cross-section of one embodiment of a guidewire.

FIG. 6 shows a longitudinal cross-section of a distal portion of one embodiment of a guidewire of the current invention. The shaft 20 can comprise a tubular member 21. The shaft can also comprise a core member 22 with a first tapered region 23. The tubular member 21 and the core member 22 can be attached, for example at a joint 24, which can be in the first tapered region 23. At least a portion of the core member 22 can be disposed in a lumen 26 of the tubular member.

Any of a broad variety of attachment techniques and/or structures can be used to achieve the attachment(s) between the tubular member 21 and the core member 22, or between any of the structures present in the shaft 20. Some examples of suitable attachment techniques include welding, soldering, brazing, crimping, friction fitting, adhesive bonding, mechanical interlocking and the like.

Some examples of welding processes that can be suitable in some embodiments include LASER welding, resistance welding, TIG welding, microplasma welding, electron beam welding, friction welding, inertia welding, or the like. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

In some embodiments, LASER or plasma welding can be used to achieve the attachments. In LASER welding, a light beam is used to supply the necessary heat. LASER welding can be beneficial in the processes contemplated by the invention, as the use of a LASER light heat source can provide significant accuracy. It should also be understood that such LASER welding can also be used to attach other components of the device. Additionally, in some embodiments, LASER energy can be used as the heat source for soldering, brazing, or the like for attaching different components or structures of the guidewire together. Again, the use of a LASER as a heat source for such connection techniques can be beneficial, as the use of a LASER light heat source can provide substantial accuracy. One particular example of such a technique includes LASER diode soldering.

Additionally, in some other example embodiments, attachment may be achieved and/or aided through the use of a mechanical connector or body, and/or by an expandable alloy, for example, a bismuth alloy. Some examples of methods, techniques and structures that can be used to interconnect different portions of a guidewire using such expandable material are disclosed in a U.S. patent application Ser. No. 10/375,766 filed Feb. 26, 2003 (Pub. No. U.S. 2004/0167441), which is hereby incorporated herein by reference. Some methods and structures that can be used to interconnect different sections are disclosed in U.S. Pat. No. 6,918,882, and U.S. patent application Ser. No. 10/086,992 filed Feb. 28, 2002 (Pub. No. U.S. 2003/0069521), which are incorporated herein by reference.

As shown in FIG. 6, the core member 22 can extend through the entire length of the lumen 26. Alternatively, the core member 22 could extend only along a portion of the lumen 26. For example, the core member 22 can extend only to the joint 24, or at least about 25%, or at least about 50%, or at least about 75% or more, through the lumen 26. If the core member extends through only a portion of the lumen 26, a wire extension can also be attached to the end of the core member 22 (this configuration will be discussed in more detail below).

Additionally, the tubular member 21 and the core member 22 may be sized and/or shaped or otherwise adapted and/or configured such that a space or gap 27 can be defined between at least a portion of the outer surface of the core member 22 and the inner surface of the tubular member 21. For example, the tubular member 21 can include an inner diameter that is greater than the outer diameter of the core member 22 that is disposed therein. As such, the tubular member 21 can be disposed about the core member 22, or a portion thereof, such that the space or gap 27 is defined therebetween. In some embodiments, the gap or space 27 remains open or unfilled by any other structure of the device 1 along substantially the entire length of the core member 22 that is disposed in the tubular member 21, with the exception of the joint 24 or the attachment to a distal tip 25, or both.

In some embodiments, the gap or space 27 can extend between the outer surface of the core member 22 and the inner surface of the tubular member 21 along the length of the tubular member 21 in the range of about 50% or greater, about 75% or greater, about 90% or greater, or about 95% or greater of the entire length of the tubular member 21. However, in other embodiments, other attachment points between the core member 22 and the tubular member 21 may be used, and as a result, multiple gaps or spaces may be created that may be separated by these additional attachment points, which may, in effect, fill portions of the gap or space 27. Such multiple gaps or spaces may still collectively extend along a substantial portion of the length of the tubular member 21, for example, in percentages of the total length as given above.

The tubular member 21 can also extend along differing amounts of the length of the core member 22. For example, the tubular member 21 can extend along about 25% or less, about 50% or less, about 75% or less, about 90% or less, or about 95% or less of the entire length of the core member 22. As such, the tubular member can act to reinforce or impart desired properties, such as torsional or pushable rigidity, to the shaft 10, but the gap or space 27 can allow at least the portion of the core member 22 surrounded by the gap or space 27 to move laterally within the lumen 26. In yet other embodiments, one or more other structures, such as one or more coils, ribbons, bands, marker members or the like, may be disposed within and fill portions of the gap 27.

The outer diameter of the tubular member 21 proximate the joint 24 can be substantially the same as the outer diameter of the core member 22 proximal of the joint 24. The outer diameter of the tubular member 21 can be substantially constant along its length. The outer diameter of the core member 22 can also be substantially constant proximal of the joint 24. If the outer diameter of the core member 22 proximal the joint 24 and the outer diameter of the tubular member 21 are substantially the same and constant, the entire length of the guidewire can have a substantially constant outer diameter. In another embodiment, if the outer diameter of the tubular member 21 or the core member outer diameter proximal of the joint 24, or both, are tapered, the guidewire can have a tapered configuration (such tapering is discussed further below).

Figure 7:
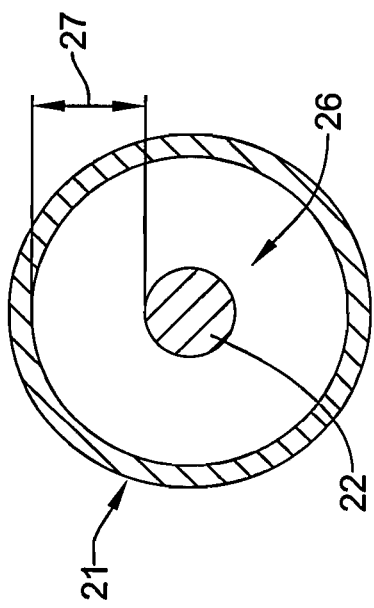
FIG. 7 is an axial cross-section at a longitudinal position along FIG. 6.
Figure 8:
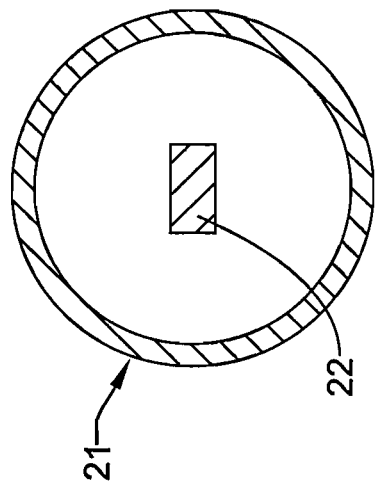
FIG. 8 is another axial cross-section at another longitudinal position along FIG. 6.

Referring again to FIG. 6, the core member 22 can be of a solid, round cross-section. The cross-section of the core member 22 could also be round, flattened, oval, rectangular, square, polygonal, and the like, or other such various cross-sectional geometries. Alternatively, the cross-sectional shape of the core member 22 could change along its length. For example, FIGS. 7 and 8 show cross-sections at two longitudinal locations along the guidewire of FIG. 6. These Figures show the core member 22 changing from a circular cross-section to a flattened or rectangular cross-section. Part or all of the core member 22 could also have a hollow cross-section. The portion of the core member 22 having a hollow cross-section can define a lumen from a proximal region to a distal region. Such a lumen could allow for passage of another device through the guidewire or allow for fluid communication along all or a portion of the length of the guidewire.

The inner and outer surfaces of the tubular member 21 can have a round cross-section, as shown in FIGS. 7 and 8. These surfaces can also have other cross-sections, such as round, flattened, oval, rectangular, square, polygonal, and the like, or other such various cross-sectional geometries. Alternatively, the cross-sectional shape of the tubular member 21 could change along its length, and the tubular member 31 can have different cross-sectional geometries on its inner and outer surfaces.

The shaft 20 may also include a distal tip 25 disposed at the distal end thereof. The distal tip 25 may include any of a broad variety of tip structures and/or assemblies, and may be adapted and/or configured to provide certain characteristics, such as atraumatic or flexibility characteristics, to the distal end of the shaft 20. The distal tip 25 can be formed from a variety of different materials, depending on desired performance characteristics. In some embodiments, the distal tip 25 can include a generally or partially rounded structure to provide an atraumatic element on the distal end of the shaft 20. In some embodiments, the distal tip 25 can be formed of a material such as a metallic material that is amenable to being welded, soldered, or otherwise attached to the distal end of the shaft 20. For example, in some embodiments, the distal tip 25 can be a solder tip or solder ball that is disposed via soldering at the distal end of the device 1 and forms an atraumatic rounded portion. In other embodiments, the distal tip 25 can be a prefabricated, or partially prefabricated structure that is thereafter attached to the distal end of the device using suitable attachment techniques, such as welding, soldering, brazing, crimping, friction fitting, adhesive bonding, mechanical interlocking and the like. A variety of different processes, such as soldering, deep drawing, roll forming or metal stamping, metal injection molding, casting and the like can be used to form such distal tip structures.

Figure 9:
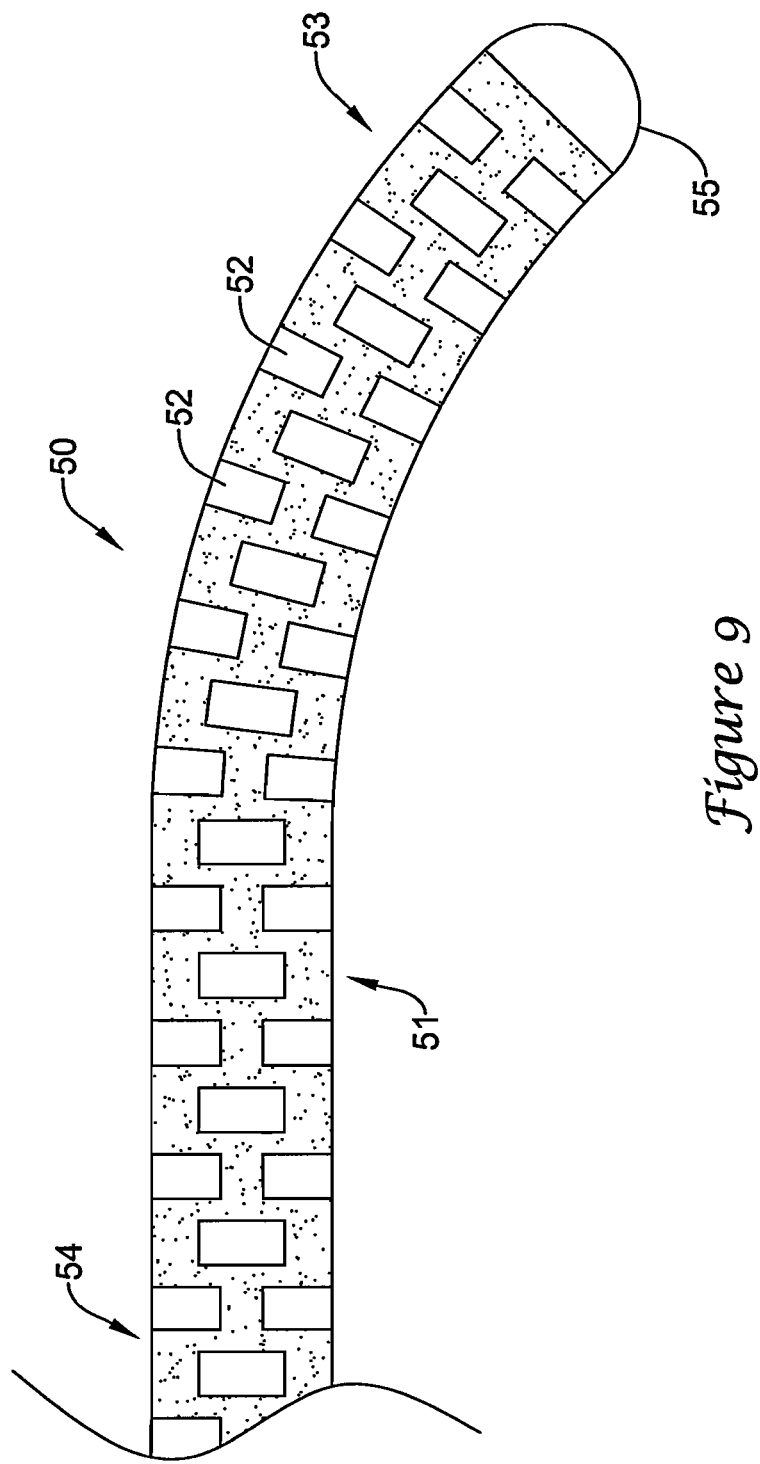
FIG. 9 is a perspective view of one embodiment of a distal portion of a guidewire that has incorporated a tubular member.

In the embodiments shown in FIGS. 5, 6 and 9, the distal tip 25 includes a rounded structure, such as a metallic or solder tip that is attached, for example, to the distal end of the tubular members (21, 51) or the distal end of the core member 22, or both (as shown in FIG. 6) and/or to other structures near or at the distal end of the shaft 20. As such, in the embodiments shown, both the tubular member 21 and the core member 22 extend to and/or into the distal tip 56, but as discussed above, this is not necessary in all embodiments. Additionally, other components, such as a ribbon, coil, marker band, centering ring, or the like may also be part of or be disposed adjacent the tip or other portions of the shaft 20. In one embodiment, a wire or ribbon can be attached to the distal end of the core member 22. This wire or ribbon can extend to and in some cases can be attached to the distal tip 25. The wire ribbon can have a cross-section shape of round, flattened, oval, rectangular, square, polygonal, and the like, or other such various cross-sectional geometries, or the cross-sectional shape can change along the length of the ribbon.

The tip construction can also include an elongate flexible member such as a helical coil or a polymer sheath, disposed within the lumen 26 of the tubular member 21 and disposed about at least a portion of the core member 22. The flexible member can be a helical coil. Such a coil may act to reinforce the distal tip of the device, and/or can act as a radiopaque marker, or both. The coil can be formed of or comprise wire or ribbon that has a solid cross-section, and that can include any of a variety of cross-sectional shapes, including round, oval, flat, ribbon-shaped, or any other suitable shape or a combination thereof. The coil can be made of a variety of materials, including metals, alloys, plastics, or other suitable materials, including radiopaque materials, many of which were discussed above. Some examples of other suitable tip constructions and structures that can be used are disclosed in U.S. Pat. No. 6,918,882, and U.S. patent application Ser. No. 10/086,992 filed Feb. 28, 2002 (Pub. No. U.S. 2003/0069521), which are incorporated herein by reference. In addition, coils as described above or other reinforcement members can be disposed about the areas of the shaft in which the flexibility is changing in order to reinforce these changes in flexibility.

The guidewire can also change in flexibility along its length. The guidewire can be more flexible in a distal part of the guidewire than in a proximal part of the guidewire in order to facilitate navigation of tortuous pathways within a patient's vasculature. The change in flexibility can result from a change in the geometry, cross-sectional area or materials of construction of the core member 22 or a change in the shape, cross-sectional area or materials of construction of the tubular member 21, or any combination of these changes.

Accordingly, core member and/or tubular member 21/22 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness/flexibility characteristics. It can be appreciated that essentially any portion of shaft 20 and/or core and/or tubular members 21/22 may be tapered, and the taper can be in either the proximal or the distal direction. The core and/or tubular members 21/22 may include one or more portions where the outside diameter is narrowing and one or more portions where the outside diameter remains essentially constant. The number, arrangement, size and length of the narrowing and constant diameter portions can be varied to achieve the desired characteristics, such as flexibility and torque transmission characteristics.

For example, in the embodiment shown in FIG. 6, the core member 22 becomes more flexible in the distal region 28 than in the proximal region 29. This variation in flexibility can be achieved, for example, by reducing the cross-sectional area along the length of the core member 22 as it extends distally. In some example embodiments, the outer diameter of the core member 22 can be in the range of about 0.005 inch to about 0.04 inches. However, it should be appreciated that other sizes may be utilized without departing from the spirit of the invention.

The shape of the core member 22, including any tapered and/or constant diameter portions, may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing the structure wire during the grinding process. In some embodiments, centerless grinding can be achieved using a Royal Master HI-AC centerless grinder. Some examples of suitable grinding methods are disclosed in U.S. patent application Ser. No. 10/346,698 filed Jan. 17, 2003 (Pub. No. U.S. 2004/0142643), which is herein incorporated by reference.

Also in some embodiments, portions of the core member 22 may be flattened, for example, to provide for desired flexibility characteristics, or to provide an attachment point for other structure. For example, the core member 22 could include a flattened portion in the distal region 28 as shown in FIG. 8. For example, the distal most about 0.05 inch to about 1 inch of the distal region 28 can be flattened to define generally parallel opposed surfaces, and to have a thickness in the range of about 0.0005 inch to about 0.003 inch.

The tubular member 21 may also include one or more tapers or tapered regions, and one or more constant diameter sections, or may generally include a constant inner and/or outer diameter. Any tapers and/or constant diameter can extend in either the proximal or the distal direction, for example, to achieve the desired flexibility/stiffness characteristics. The tapers and/or any constant diameter sections may be manifested in variations and/or inconsistencies in the outer diameter, inner diameter, and/or wall thickness of the tubular member 21. Any tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness/flexibility characteristics.

In some embodiments, the tubular member 21 can have an inner diameter, defining the lumen 26, that is in the range of about 0.01 inch to about 0.06 inch in size, and in some embodiments, in the range of about 0.02 inch to about 0.035 inch in size. Additionally, in some embodiments, the tubular member 21 can have an outer diameter that is in the range of about 0.015 inch to about 0.07 inch in size, and in some embodiments, in the range of about 0.02 inch to about 0.04 inch in size. It should be understood however, that these and other dimensions provided herein are by way of example embodiments only, and that in other embodiments, the size of the inner and outer diameter of the tubular member 21 and other elements of the medical device can vary greatly from the dimensions given, depending upon the desired characteristics and function of the device.

The tubular member 21 can also include other structure or otherwise be adapted and/or configured to achieve a desired level of stiffness, torqueability, flexibility, and/or other characteristics. The desired stiffness, torqueability, lateral flexibility, bendability or other such characteristics of the tubular member 21 can be imparted, enhanced, or modified by the particular structure that may be used or incorporated into the tubular member 21. As can thus be appreciated, the flexibility of the tubular member can vary along its length, for example, such that the flexibility can be higher at the distal end relative to the proximal end, or vice versa. However, in some embodiments, the tubular member can have a substantially constant flexibility along the entire length thereof.

One manner of imparting additional flexibility is to selectively remove material from portions of a tubular member (for example, tubular member 21). For example, with reference to FIG. 9, the tubular member 51 may include a thin wall tubular structure including one or more, or a plurality of, apertures 52, such as grooves, cuts, slits, slots, or the like, formed in a portion of, or along the entire length of, the tubular member 51. The apertures 52 can be formed in essentially any known way. For example, apertures 52 can be formed by methods such as micro-machining, saw-cutting, laser cutting, grinding, milling, casting, molding, chemically etching or treating, or other known methods, and the like. In some such embodiments, the structure of the reinforcing member 52 is formed by cutting and/or removing portions of the tube to form apertures 52.

In some embodiments, the apertures 52 can completely penetrate the body wall of the tubular member 51 such that there is fluid communication between a lumen (for example, lumen 26) and the exterior of the tubular member 51 through the apertures 52. In some embodiments, the apertures 52 may only partially extend into the body wall of the tubular member 51, either on the interior or exterior surface thereof. Some other embodiments may include combinations of both complete and partial apertures 52 through the body wall of the tubular member 51. The shape and size of the apertures 52 can vary, for example, to achieve the desired characteristics. For example, the shape of apertures 52 can vary to include essentially any appropriate shape, such as squared, round, rectangular, pill-shaped, oval, polygonal, elongate, irregular, spiral (which may or may not vary in pitch), or other suitable means or the like, and may include rounded or squared edges, and can be variable in length and width, and the like.

In some embodiments, some adjacent apertures 52 can be formed such that they include portions that overlap with each other about the circumference of the tubular member 51. In other embodiments, some adjacent apertures 52 can be disposed such that they do not necessarily overlap with each other, but are disposed in a pattern that provides the desired degree and/or direction of lateral flexibility. For example, the apertures 52 can be arranged in a symmetrical pattern, such as being disposed essentially equally on opposite sides about the circumference of the tubular member 51, or equally spaced along the length of the tubular member 51.

As can be appreciated, the spacing, arrangement, and/or orientation of the apertures 52 can be varied to achieve the desired characteristics. For example, the number, proximity (to one another), density, size, shape and/or depth of the apertures 52 along the length of the tubular member 51 may vary in either a stepwise fashion or consistently, depending upon the desired characteristics. For example, the number or proximity of apertures 52 to one another near one end of the tubular member 51 may be high, while the number or proximity of apertures 52 to one another near the other end of the tubular member 51, may be relatively low, or vice versa. In some embodiments, the distal region 53 of the tubular member 51 may include a greater density of apertures 52, while the proximal region 54 of the tubular member 51 may include a lesser density of apertures, or may even be devoid of any apertures 52. As such, the distal region 53 can have a greater degree of lateral flexibility relative to the proximal region 54. It should be understood that similar variations in the size, shape and/or depth of apertures 52 along the length of the tubular member 51 can also be used to achieve desired flexibility differences there along.

In the embodiment shown in FIG. 9, the apertures 52 are disposed in a generally uniform pattern along the length of the tubular member 51 with a greater aperture density at a distal portion of the tubular member 51 compared to a proximal portion. In this embodiment, the apertures 52 can have a length and a width, and the length of the apertures extend generally perpendicular to the longitudinal axis of the tubular member 51. In other words, the apertures 52 can have a major axis extending along their length that extends radially about the longitudinal axis of the body 51, and the major axis is generally perpendicular to the longitudinal axis of the tubular body 51.

Additionally, in the embodiment shown, the apertures 52 are formed in groups of two, wherein each of the two apertures 52 in the group is disposed at a similar longitudinal point along the length of the tubular member 51, but on opposite side of the tubular member about the circumference thereof. Adjacent pairs of apertures 52 can be rotated by 90 degrees, or by less than 90 degrees, for example 80, 85 or 89 degrees. It should be understood, however, that in other embodiments the arrangement of the apertures can be varied to achieve the desired characteristics along the length of the tubular member 51. For example, instead of pairs, only a single aperture, or more than two apertures, may be located at certain points along the length of the device. Additionally, the major axis of the apertures may be disposed at different angles, not necessarily perpendicular to the longitudinal axis of the tubular member 51.

Collectively, this Description illustrates that changes in the arrangement, number, and configuration of apertures 52 may vary without departing from the scope of the invention. For example, the tubular body could have no apertures 52. Some additional examples of arrangements of apertures, such as cuts or slots, formed in a tubular body are disclosed in U.S. Pat. Nos. 6,428,489, and in 6,579,246, both of which are incorporated herein by reference. Also, some additional examples of arrangements of cuts or slots formed in a tubular body for use in a medical device are disclosed in a U.S. patent application Ser. No. 10/375,493 filed Feb. 28, 2003 (Pub. No. U.S. 2004/0167437), which is incorporated herein by reference.

The flexibility characteristics of the tubular member 21 could also be achieved using other methods, such as by the addition of material and/or one or more reinforcement members to certain portions of the tubular member 21 and/or core member 22. One additional method of imparting flexibility in the tubular member 21 or core member 22 is to make a helical cut in these members. The helical cut could extend through the entire thickness of the wall of the tubular member 21, or only partially through the wall. The helical cut can also have a pitch, and the pitch can be constant or can vary along the length of the tubular member. For example, the pitch of the helical cut can change, making adjacent cuts of the helical cut closer together at the distal end of the member compared to the proximal end of the member, or vice versa.

Those of skill in the art and others will recognize that the materials, structures, and dimensions of the core member 22 and the tubular member 21 are dictated primarily by the desired characteristics and function of the final guidewire, and that any of a broad range of materials, structures, and dimensions can be used. It is also noted that any of the flexible tubular structures mentioned herein can be incorporated into any of the medical device embodiments described herein.

For example, the tubular member 21 and core member 22 may be formed of any materials suitable for use, dependent upon the desired properties of the device 1. Some examples of suitable materials include metals, metal alloys, polymers, composites, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals or metal alloys that are suitable for metal joining techniques such as welding, soldering, brazing, crimping, friction fitting, adhesive bonding, etc. The particular material used can also be chosen in part based on the desired flexibility requirements or other desired characteristics.

In some embodiments, the core member 22 and tubular member 21 can be made of the same material, or in some embodiments, they can be made of different materials, or each can include portions or sections thereof that are made of different materials. The material used to construct the different portions of the shaft (10, 20) can be chosen to impart varying characteristics, for example, flexibility and stiffness characteristics, to different portions of the shaft (10, 20).

For example, in some embodiments, the core member 22 may include or be formed of relatively stiff material such as a stainless steel wire or Inconel. Alternatively, core member 22 may include or be formed of a metal or metal alloy such as a nickel-titanium alloy, nickel-chromium alloy, nickel-chromium-iron alloy, cobalt alloy, or other suitable material. In many embodiments, the material used to construct the core member 22 may be selected to be relatively stiff, for example, for pushability and/or torqueability.

In some embodiments, the tubular member 21 may include or be formed of a relatively flexible material such as a material exhibiting superelastic and/or shape memory properties. For example, the tubular member 21 could be constructed at least in part from a metal alloy (for example, Nitinol or any other shape memory/superelastic alloys described herein) that can exhibit both shape memory and superelastic characteristics under certain conditions.

In some particular embodiments, the tubular member 21 comprises a material (such as a metal alloy, for example, Nitinol) that can exhibit both shape memory and superelastic characteristics and the core member 22 can comprise a stainless steel wire. The stainless steel wire provides for good transmission of forces down the length of the device, while the tubular member 21 can provide additional support for the distal portions of the core member 22. A tubular member 21 of a superelastic/shape memory material can provide for some additional elasticity in the distal portion of the device.

As mentioned earlier, some materials, and specifically some metal alloys, have shape memory and/or superelastic characteristics affected by the temperature of use. As discussed in the text above, metal alloys or other materials with shape memory and/or superelastic properties, such as Nitinol, can have $A_f$, $A_s$, $M_f$ and $M_s$ temperatures. The relationship between these critical temperatures and the temperature of use can be determinative of the properties of the materials. For example, if the temperature of use (referred to herein as the $T_m$) is above the $A_f$ temperature, the material can exhibit superelastic characteristics when it is stressed. If $T_m$ is above $A_s$ temperature but below $A_f$ temperature, then the material can exhibit some superelastic characteristics if it is deformed and, if the material is subsequently heated to a $T_m$ above the $A_f$ temperature, it can exhibit shape memory characteristics and may be able to return to its original shape and size. Further, if the $T_m$ is below the $A_s$ and $A_f$ temperatures, then the material can either be fully martensitic or form a full martensite phase when placed under stress, and the material may not exhibit superelastic characteristics as long as the $T_m$ is kept below the $A_s$ and $A_f$ temperatures (although the material may exhibit shape memory characteristics if the $T_m$ is subsequently raised above the $A_s$ and/or $A_f$ temperatures). This material may be able to be deformed and maintain its deformed shape if it is not subsequently exposed to a catalyst such as heat. In another example, if the $T_m$ is below the $M_s$ and/or the $M_f$ temperatures, then the unstressed material may be partially or totally in the martensite phase. In such a scenario, the material, when deformed, may substantially remain deformed. Again, such material can exhibit shape memory if later heated above the $A_s$ and/or the $A_f$ temperatures.

In some embodiments of the current invention, the tubular member 21 can have different zones. The different zones can be located at different longitudinal positions along the tubular member 21. These zones can comprise different materials or metal alloys or the same material or metal alloy. The zones can comprise material(s) that have critical temperatures $M_f$, $M_s$, $A_s$ and $A_f$, as described in this application.

In some embodiments, some of the zones (which can be called the deformable zones) can have $M_s$ and $M_f$ temperature that are above the $T_m$ (again, $T_m$ is the temperature (or temperature range) at which the device may be used) while other zones (which can be called the elastic zones) can have an $A_s$ temperature that is below the $T_m$, but an $A_f$ temperature that remains above the $T_m$. In such a case, as long as the temperature is maintained at or within the $T_m$, the deformable zones can be deformed and they can substantially maintain the deformed shape, while the elastic zones can be deformed and may at least partially return to their original shape. In some embodiments, similar properties can result if the $A_s$ temperature of the deformable zone(s) is above the $T_m$ and the $M_f$ and/or $M_s$ temperatures are below the $T_m$ and the elastic zone(s) are as described above. In this case, similar physical properties can result (deformable zone(s) substantially maintaining their deformed shapes and elastic zones having at least partial elastic properties), but the deformable zones may form stress-induced martensite when they are deformed.

In some other embodiments, the properties and materials of construction of the deformable zone(s) can have the same properties and materials as described above, while the elastic zone(s) can have similar or the same construction as described above, but can instead have both $A_s$ and $A_f$ temperatures that are below the $T_m$. In such a case, the elastic zones can have more pronounced elastic properties.

In other embodiments, the $A_f$ temperature can be just below the $T_m$ in the deformable zone(s), whereas the $A_f$ temperature can be further below the $T_m$ in the elastic zone(s). Although all the zone(s) in such an example will have some elastic properties, the deformable zone(s) will be less elastic than the elastic zone(s). As an example, the $A_f$ temperature of the deformable zone(s) can be within 5° C. of the $T_m$ and the $A_f$ temperature of the elastic zone(s) can be at least 10° C., 15° C. or 20° C. below the $T_m$.

In any of the embodiments in this application, the $T_m$ can generally be the temperature or temperature range of the particular use for which a typical medical device may be used. Alternatively, the $T_m$ can be the normal human body temperature (37° C.), or 40° C., 42° C., 45° C., 50° C. or 55° C., or the $T_m$ can be a temperature range of ±5 degrees Celsius or ±10 degrees Celsius around any of the above temperatures. Other temperature ranges that can be represented by $T_m$ can be 10° C.-37° C., 10° C.-40° C., 10° C.-42° C., 10° C.-45° C., 10° C.-50° C., 10° C.-55° C., 15° C.-37° C., 15° C.-40° C., 15° C.-42° C., 15° C.-45° C., 15° C.-50° C., 15° C.-55° C., 27° C.-32° C., 27° C.-37° C., 27° C.-40° C., 27° C.-42° C., 27° C.-45° C., 27° C.-50° C., 27° C.-55° C., 32° C.-37° C., 32° C.-40° C., 32° C.-42° C., 32° C.-45° C., 32° C.-50° C., 32° C.-55° C., 37° C.-40° C., 37° C.-42° C., 37° C.-45° C., 37° C.-50° C., 37° C.-50° C., 37° C.-55° C., 40° C.-42° C., 40° C.-45° C., 40° C.-50° C., and 40° C.-55° C.

In any of the embodiments described in this application, the different zones can be made from different materials or the different zones can be made from substantially the same material that has been treated to have the different properties described above. For example, the zones can comprise substantially the same metal alloy (such as Nitinol or any of the other shape memory and/or superelastic alloys mentioned in this application) that has been treated differently at the different zones, or the zones could comprise different metal alloys (such as different alloys of Nitinol, or any other suitable alloys listed in this application). The deformable zone(s) can be located at the distal end, at a distal portion, an intermediate portion, a proximal portion, or any combination thereof, of the tubular member 21. There can be one or more deformable zones and elastic zones; for example, there can be 1, 2, 3, 4, 5, or 6 deformable zones and/or 1, 2, 3, 4, 5 or 6 elastic zones. The deformable zones can allow a manufacturer or operator to change the shape of the tubular member in order to match a medical device to the particular use and anatomy of a patient. As an example, the deformable zones can be formed along the medical device at a location that corresponds to a particularly sharp bend in a patient's vasculature. As another example, the distal end of a medical device can be shaped to facilitate navigation of a tortuous pathway within a patient's vasculature.

Although the relationship between only the first deformable and elastic zones are described above, any other deformable zone(s) and elastic zone(s) can have a similar relationship relative to the $T_m$ and the first deformable and elastic zones. For example, if the first deformable zone has an $A_f$ temperature above the $T_m$ and the first elastic zone has an $A_f$ temperature below the $T_m$, then a second deformable zone can also have an $A_f$ temperature above the $T_m$, and a second elastic zone can also have an $A_f$ temperature below the $T_m$. In embodiments with two or more deformation zones and/or two or more elastic zones, the deformable zones can differ from one another and the elastic zones can differ from one another. Each of the elastic zones can individually have any of the characteristics described herein and each of the deformable zones can individually have any of the characteristics described herein.

In another example embodiment, the elastic zone(s) of any of the above embodiments can be linearly elastic in conjunction with any of the deformable zone(s) that are described in this application. The material in the elastic zone(s) can be a material that may have shape memory and/or superelastic properties under certain conditions but can be treated to be linearly elastic. Alternatively, the material in the elastic zone(s) can be material that is characteristically linear elastic material. In an alternative embodiment, any of the deformable zones described in this application can have shape memory characteristics within the range of temperatures of use for the medical device, allowing these zones to return to an initial shape and configuration when exposed to a temperature near the top of a range of use temperatures ($T_m$), but remaining deformed in the bottom of this temperature range ($T_m$).

The lengths of the elastic and deformable zones can vary. For example, a deformable zone on the distal end of a medical device can be between 0.1 inches and 7 inches long; for example the deformable zone can be 0.1, 0.2, 0.25, 0.3, 0.4, 0.5, 0.75, 1, 1.25, 1.5, 1.75, 2, 2.5, 3, 3.5, 4, 5, 6 or 7 inches long. Deformable zones that are in an intermediate portion can be of the same lengths.

In general, the tubular members described above with respect to the guidewires shown in FIGS. 5, 6 and 9 can also be applied to other elongate medical devices. Other such medical devices can be any medical devices that can commonly incorporate an elongate tubular structure, for example catheters.

Figure 10:
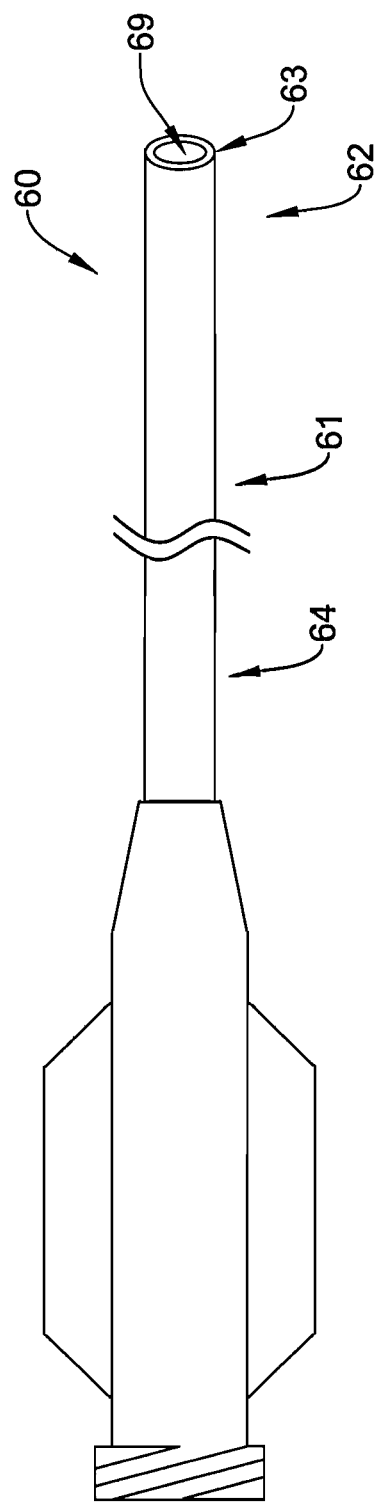
FIG. 10 is a perspective view of an embodiment of a catheter.

Referring now to FIG. 10, one embodiment of a catheter shaft 60 is shown in perspective view. The catheter shaft 60 comprises a tubular member 61, which has a proximal portion 64, a distal portion 62, and an intermediate portion therebetween. The tubular member 61 also has a distal end 63, and the tubular member 61 defines a lumen 69. In one embodiment, the tubular member 61 can have similar structure and characteristics as the tubular member 21 described above with respect to guidewires. Specifically, the shapes and possible structures for varying the flexibility of the tubular member 21 can also be used in the context of the tubular member 61. In addition, the distal end 63 of the catheter shaft can have a rounded, soft, and/or more flexible portion in order to prevent traumatic interaction with a body vessel of a patient.

It is contemplated that the tubular member 61 can comprise any of the tubular designs described herein. The tubular member 61 can also have deformable and elastic zones, similar to those described herein. For example, the number, physical properties and configurations of the deformable and elastic zones can be similar to those described above with respect to the tubular member 21.

Portions or all of the catheter shafts or the guidewires described herein may in some cases be doped with, coated or plated with, made of, or otherwise include a radiopaque material. Radiopaque materials are understood to be materials capable of producing a relatively bright image on a fluoroscopy screen or another imaging technique during a medical procedure. This relatively bright image aids the user of the devices in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, in some instances a degree of MRI compatibility can be imparted into the devices of this application. For example, to enhance compatibility with Magnetic Resonance Imaging (MRI) machines, all or portions of the catheter shafts of the guidewires can be made in a manner that would impart a degree of MRI compatibility. For example, all or a portion of the catheter shafts or guidewires may be made of a material that does not substantially distort the image and create substantial artifacts (artifacts are gaps in the image) during MRI imaging. Certain ferromagnetic materials, for example, may not be suitable because they may create artifacts in an MRI image. All or a portion of the catheter shafts or guidewires may also be made from a material that the MRI machine can image. Some materials that exhibit these characteristics include, for example, tungsten, Elgiloy, MP35N, nitinol, and the like, and others, or combinations or alloys thereof.

The lengths of the catheter shafts and/or the guidewires of this application are typically dictated by the useful length and flexibility characteristics desired in the final device. For example, these devices may have a total length in the range of about 25 to about 350 centimeters or more. It can be appreciated that the lengths of the individual components can be adapted such that the desired length, flexibility, torqueability, and other characteristics are achieved, and that alterations in these lengths can be made without departing from the spirit of the invention.

Additionally, in some embodiments, a coating, for example a lubricious (e.g., hydrophilic) or other type of coating may be applied over portions or all of the medical devices or structures discussed above. For example, such a coating may be applied over portions or the entire length of the catheter shaft 60 or the guidewire shafts of FIGS. 5, 6 and 9, over part or all of the tubular members of these shafts, over a distal tip (e.g., 25, 55), a distal portion, or other portions of the shafts. Hydrophobic coatings such as fluoropolymers, silicones, and the like provide a dry lubricity which improves guide wire handling and device exchanges. Lubricious coatings improve steerability and improve lesion crossing capability. Suitable lubricious polymers are well known in the art and may include hydrophilic polymers such as, polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions are coated with a fluoropolymer, such as polytetrafluoroethylene (PTFE).

The use of a coating layer in some embodiments can impart a desired flexibility to the catheter shafts, guidewire shafts, and/or the tubular members described in this application. Choice of coating materials may vary depending upon the desired characteristics. For example, coatings with a low durometer or hardness may have very little effect on the overall flexibility of the devices. Conversely, coatings with a high durometer may make for a stiffer and/or less flexible shaft. Where a tubular member has apertures or a helical cut formed through the wall of the tubular member, a coating can seal off all or some of the apertures or the helical cut.

Another embodiment of the current invention is a method of manufacturing a guidewire, for example the guidewire of FIG. 6. A core member and a tubular member can be provided, and a distal portion of the core member can be disposed at least partially inside a lumen of the tubular member. A proximal portion of the tubular member can be attached to the core member, for example using one of the techniques discussed in this application. Further, the tubular member can comprise a material that exhibits shape memory and/or superelastic properties, for example a metal alloy such as Nitinol or other materials or alloys discussed herein. The tubular member could comprise one such material, or it could comprise different zones with different such materials. The tubular member can have a deformable zone(s) and an elastic zone(s) as discussed herein, and these zones can result from different zones comprising different materials. Further, the deformable and elastic zones can be formed by treating portions of the tubular member, for example as discussed in this application. The deformable zone(s) can be treated to alter the properties in these areas, or the elastic zone(s) can be treated to alter the properties of these areas, or both the deformable and elastic zones could be treated to alter the properties of these areas. A deformable zone can be located at a distal portion, a distal tip and/or an intermediate portion, or at any other portion of a medical device as discussed herein. Further, the tubular member can be treated before or after it is attached to a core member or any other element of the medical device. Such a medical device can also have a distal tip formed on the end, and any tubular member could also have apertures formed in it, for example as described in this application.

In one example embodiment, the deformable zone(s) can be heat treated, for example in order to raise one or more of the critical temperatures of a metal alloy. Further, or in lieu of treating the deformable zone(s), the elastic zone(s) could be treated in order to impart differential properties between the elastic and deformable zones. As an example, the elastic zone(s) can be treated in order to make them linear elastic.

Further, a tubular member for a catheter or other medical device can be formed using the above method of forming a tubular member for a guidewire.

In addition, during manufacture, a deformable portion(s) of the tubular members described in this application could be shaped to a predetermined shape in preparation for a medical procedure.

Alternatively, a method of use can include providing one of the structures described in this application and the treating portions of the tubular members of these structures in order to form deformable and elastic zones. These methods can include any of the methods and locations of treatment as described herein. Another method of use can further include the steps of providing one of the structures described in this application that contain deformable zones and, in a clinical setting, deforming the deformable zones of the tubular member to a predetermined shape in preparation for a medical procedure. Additionally, these methods of use can include providing one of the structures described in this application and, in a clinical setting, both treating portions of the tubular members of these structures in order to form deformable and elastic zones and deforming the deformable portions of the tubular member to a predetermined shape in preparation for a medical procedure.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What we claim is:

1. An intra-luminal medical device comprising:
an elongate tubular member formed from a single metal alloy and having a lumen therethrough with proximal and distal portions, the distal portion of the elongate tubular member configured to be inserted into and advanced through a vessel, the tubular member having a plurality of longitudinally spaced apertures in the distal portion and one or more zones of metal alloy, each zone of metal alloy having an $A_f$ temperature, wherein the tubular member has a first $A_f$ in a first zone of metal alloy and a second, higher $A_f$ in a second zone of metal alloy, wherein the first zone of metal alloy is proximal of the second zone of metal alloy, wherein the first $A_f$ and the second $A_f$ are set such that, when at or near a normal body temperature of a human body and free of stress, the first zone of metal alloy is austenitic and the second zone of metal alloy is martensitic; and
wherein the proximal portion has superelastic characteristics and the distal portion has linear elastic characteristics.

2. The intra-luminal device according to claim 1, wherein the second zone is located proximal of a distal end of the tubular member.

3. The intra-luminal device according to claim 1, wherein the tubular member further comprises a third zone of metal alloy with a third $A_f$ lower than the second $A_f$ of the second zone.

4. The intra-luminal device according to claim 1, further including an elongate core member having distal and proximal regions, the core member at least partially disposed within the lumen of the elongate tubular member.

5. The intra-luminal device according to claim 4, wherein the proximal portion of the tubular member is attached to an intermediate region of the core member, the intermediate region disposed between the proximal and distal portions of the elongate tubular member.

6. The intra-luminal medical device according to claim 1, wherein the apertures are slots, and the tubular member has a higher density of slots at the distal portion compared to the proximal portion.

7. The intra-luminal medical device according to claim 4, further comprising an atraumatic distal tip, the tip forming a rounded shape on a distal end of the tubular member.

8. The intra-luminal medical device according to claim 7, wherein the distal tip is attached to a distal end of the tubular member.

9. The intra-luminal device according to claim 4, further comprising an atraumatic distal tip, the tip forming a rounded shape on a distal end of the device, the tip connected to a distal end of the core member.

10. The intra-luminal device according to claim 4, wherein the proximal portion of the tubular member is attached to the core member at an attachment zone, and distal of the attachment zone a space is formed between an inner surface of the tubular member and an outer surface of the core member when the device is in a straight configuration.

11. The intra-luminal device according to claim 1, wherein the tubular member has a wall defining the lumen, and the wall has a smaller thickness in the distal portion compared to the proximal portion.

12. The intra-luminal device according to claim 4, wherein the core member has a first diameter in a proximal region and a second, smaller diameter in the distal region.

13. The intra-luminal device according to claim 12, wherein the core tapers in a step-wise fashion, and the tubular member is attached to the core member at a step-wise taper in the core member.

14. The intra-luminal device according to claim 4, wherein the core member has a solid cross-section.

15. The intra-luminal device according to claim 4, wherein the length of the second zone is less than 0.5 inches.

16. The intra-luminal device according to claim 4, wherein the length of the second zone is between 0.1 and 0.5 inches.

17. The intra-luminal device according to claim 1, wherein the tubular member comprises a nickel-titanium alloy.

18. The intra-luminal device according to claim 17, wherein the tubular member comprises a single nickel-titanium alloy.

19. The intra-luminal device according to claim 1, wherein, when no stress is applied to the elongate member, the first $A_f$ is lower than 32° C. and the second $A_f$ is higher than 37° C.

20. The intra-luminal device according to claim 1, wherein, when no stress is applied to the elongate member, the first $A_f$ is lower than 15° C. and the second $A_f$ is higher than 42° C.

21. The intra-luminal device according to claim 1, wherein, when no stress is applied to the elongate member, the first $A_f$ is lower than 15° C. and the second $A_f$ is higher than 50° C.

22. The intra-luminal device according to claim 1, wherein the one or more zones of metal alloy have an $A_s$, wherein the first zone of metal alloy of the tubular member has a first $A_s$ and the second zone of metal alloy has a second $A_s$, the first $A_s$ being lower than 15° C. and the second $A_s$ being above 42° C. when no stress is applied to the elongate member.

23. The intra-luminal device according to claim 1, wherein the one or more zones of metal alloy have a $M_f$, wherein the first zone of metal alloy has a first $M_f$ and the second zone of metal alloy has a second $M_f$, the first $M_f$ being lower than 15° C. and the second $M_f$ being above 42° C. when no stress is applied to the elongate member.

24. An intra-luminal medical device comprising:
an elongate tubular member including a proximal portion and a distal portion for insertion into a vascular system, the elongate tubular member including a lumen extending therethrough, the tubular member including a plurality of longitudinally spaced apertures located in the distal portion, wherein the distal portion of the tubular member includes at least a first zone of metal alloy and a second zone of metal alloy, the first zone of metal alloy being proximal of the second zone of metal alloy, wherein when the elongate tubular member is at a temperature of about 37 degrees Celsius and free of stress, the first zone of metal alloy is configured to be in an austenite phase and the second zone of metal alloy is configured to be in a martensite phase; and wherein the proximal portion has superelastic characteristics and the distal portion has linear elastic characteristics.

25. The intra-luminal medical device of claim 24 wherein the second zone of metal alloy is more deformable than the first zone of metal alloy.

26. The intra-luminal medical device of claim 25, wherein the tubular member further comprises a third zone of metal alloy, wherein the second zone of metal alloy is more elastic than the third zone of metal alloy.

27. The intra-luminal medical device of claim 24, further including an elongate core member having distal and proximal regions, the core member at least partially disposed within the lumen of the elongate tubular member.

28. The intra-luminal medical device of claim 27, wherein the proximal portion of the tubular member is attached to an intermediate region of the core member, the intermediate region disposed between the proximal and distal portions of the elongate tubular member.

29. The intra-luminal medical device of claim 24, wherein the apertures are slots, and the tubular member has a higher density of slots at the distal portion compared to the proximal portion.

30. The intra-luminal medical device of claim 28, further comprising an atraumatic distal tip, the tip forming a rounded shape on a distal end of the tubular member.

31. The intra-luminal medical device of claim 30, wherein the distal tip is attached to the distal end of the tubular member.

32. An intra-luminal medical device comprising:

an elongate tubular member having a proximal end, a distal end, and a lumen extending therebetween, the elongate tubular member formed from a single metal alloy having an austenitic state and a martensitic state;

wherein the transition between martensitic to austenitic starting at a temperature $A_s$ and finishing at $A_f$ and the transition between austenitic and martensitic states starting at a temperature $M_s$ and finishing at $M_f$;

the elongate tubular member further comprising:

a first zone extending distally from the proximal end of the elongate shaft, the first zone having a first $A_f$ lower than 15° C.;

a second zone extending distally from a distal end of the first zone to the distal end of the elongate tubular member, the second zone having a second Af greater than 42° C.;

wherein the first zone exhibits superelastic characteristics and the second zone exhibits linear elastic characteristics.

* * * * *

UNITED STATES PATENT AND TRADEMARK OFFICE
CERTIFICATE OF CORRECTION

Page 1 of 2

PATENT NO. : 8,728,010 B2
APPLICATION NO. : 11/509185
DATED : May 20, 2014
INVENTOR(S) : Hirshman It is certified that error appears in the above-identified patent and that said Letters Patent is hereby corrected as shown below:

In the Specification

Column 1
Line 50: after "37°C", delete "."
Line 52: before "to 45°", delete "."

Column 7
Line 9: after "about -60°C", delete "."
Line 43: after "30°C", delete "."
Line 43: after "37°C", delete "."
Line 44: after "at 500°C", delete "."
Line 45: after "at 400°C", delete "."
Line 47: after "above 500°C", delete "."
Line 49: after "above 550°C", delete "."

Column 17
Line 31: after "within 5°C", delete "."
Line 32: after "at least 10°C", delete "."
Line 32: after "15°C", delete "."
Line 33: after "or 20°C", delete "."

In Column 17, please replace line 38,
ture (37°C.),or 40°C.,42°C.,45°C.,50°C.or 55°C.,or the to read as:

--ture (37°C),or 40°C,42°C,45°C,50°C or 55°C, or the--

Signed and Sealed this
Thirtieth Day of September, 2014

Michelle K. Lee
*Deputy Director of the United States Patent and Trademark Office*

CERTIFICATE OF CORRECTION (continued)
U.S. Pat. No. 8,728,010 B2

In Column 17, please replace lines 42-50,
C.-37°C.,10°C.-40°C.,10°C.-42°C.,10°C.-45°C.,10°C.-50°C.,10°C.-55°C.,15°C.-37°C.,
15°C.-40°C.,15°C.-42°C.,15°C.-45°C.,15°C.-50°C.,15°C.-55°C.,27°C.-32°C.,27°C.-37°C.,
27°C.-40°C.,27°.-42°C.,27°C.-45°C.,27°C.-50°C.,27°C.-55°C.,32°C.-37°C.,32°C.-40°C.,
32°C.-42°C.,32°-45°C.,32°.-50°C.,32°C.-55°C.,37°C.-40°C.,37°C.-42°C.,37°C.-45°C.,
37°.-50°C.,37°C.-55°.,40°C.-42°.,40°C.-45°C.,40°C.-50°C.,and 40°C.-55°C.

to read as:

C - 37°C,10°C- 40°C,10°C- 42°C,10°C- 45°C,10°C- 50°C,10°C- 55°C,15°C- 37°C,15°C- 40°C,15°C- 42°C,15°C- 45°C,15°C- 50°C,15°C- 55°C,27°C- 32°C,27°C- 37°C,27°C- 40°C,27°C- 42°C,27°C- 45°C,27°C- 50°C,27°C- 55°C,32°C- 37°C,32°C- 40°C,32°C- 42°C,32°C- 45°C,32°C- 50°C,32°C- 55°C,37°C- 40°,37°C- 42°,37°C- 45°C,37°C- 50°C,37°C- 55°C,40°C- 42°C,40°C- 45°C,40°C- 50°C, and 40°C- 55°C.

In the Claims

Column 22
Line 41, Claim 19: after "lower than 32°C", delete "."
Line 44, Claim 20: after "lower than 15°C", delete "."
Line 47, Claim 21: after "lower than 15°C", delete "."
Line 52, Claim 22: after "above 42°C", delete "."
Line 58, Claim 23: before "and the second", delete "."
Line 58, Claim 23: after "above 42°C", delete "."

Column 24
Line 19, Claim 27: after "than 15°C", delete "."
Line 23, Claim 28: after "than 42°C", delete "."